(12) United States Patent
Suzuki (10) Patent No.: US 7,713,270 B2
(45) Date of Patent: May 11, 2010

(54) ENDOSCOPIC TREATMENT INSTRUMENT

(75) Inventor: Keita Suzuki, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 89 days.

(21) Appl. No.: 11/824,627

(22) Filed: Jul. 2, 2007

(65) Prior Publication Data

US 2008/0009856 A1    Jan. 10, 2008

(30) Foreign Application Priority Data

Jul. 4, 2006    (JP) .................. P2006-184366

(51) Int. Cl.
*A61B 18/14*    (2006.01)
(52) U.S. Cl. ................ 606/46; 606/41; 606/45
(58) Field of Classification Search ............ 606/32–52, 606/205–207
See application file for complete search history.

(56) References Cited

U.S. PATENT DOCUMENTS

| | | | | |
|---|---|---|---|---|
| 4,011,872 A | * | 3/1977 | Komiya | .............. 606/47 |
| 4,249,533 A | * | 2/1981 | Komiya | .............. 606/15 |
| 4,311,143 A | * | 1/1982 | Komiya | .............. 606/47 |
| 5,782,747 A | * | 7/1998 | Zimmon | .............. 600/104 |
| 7,294,139 B1 | * | 11/2007 | Gengler | .............. 606/206 |
| 2005/0267464 A1 | | 12/2005 | Truckai et al. | |

FOREIGN PATENT DOCUMENTS

| | | | |
|---|---|---|---|
| CH | 547103 | * | 3/1973 |
| CH | 547 103 | | 3/1974 |
| JP | 5-42167 | | 2/1993 |
| JP | 11-503041 | | 3/1999 |
| JP | 2005-80944 | | 3/2005 |
| WO | WO 96/29945 | | 10/1996 |

OTHER PUBLICATIONS

Japanese Office Action dated Jan. 19, 2010 with Translatiion.

* cited by examiner

*Primary Examiner*—Michael Peffley
*Assistant Examiner*—Ronald Hupczey, Jr.
(74) *Attorney, Agent, or Firm*—Scully, Scott, Murphy & Presser, P.C.

(57) ABSTRACT

An endoscopic treatment instrument is provided which includes: a sheath 2 having electrical insulating properties; a pair of arm portions 3A and 3B which are disposed opposite to each other, which protrude and retract with respect to the sheath 2, and which accordingly open and close to thereby hold an object to be treated; a cutting electrode 5 which is protruded from and fixed to the distal end of the sheath 2 and which supplies a high-frequency electric current when it touches the object to be treated.

6 Claims, 9 Drawing Sheets

ENDOSCOPIC TREATMENT INSTRUMENT

BACKGROUND OF THE INVENTION

1. Field of the Invention

The present invention relates to an endoscopic treatment instrument.

Priority is claimed on Japanese Patent Application No. 2006-184366, filed Jul. 4, 2006, the content of which is incorporated herein by reference.

2. Description of the Related Art

Conventionally, an endoscopic treatment instrument is used in which it is inserted in a body cavity through a channel of an endoscope to incise or cut an affected part, which is an object to be treated, of living tissue. As an example, there has been proposed an endoscopic treatment instrument in which an affected part of a patient's body is held by means of an opening and closing operation of a pair of arm portions extendable and retractable relative to an insulating sheath and then the thus-held affected part is excised or fixed by supplying thereto a high-frequency electric current or energy (see, e.g., Japanese Unexamined Patent Application, First Publication No. 5-42167).

With this endoscopic treatment instrument, even if the affected part is too large to be held by a snare or the like, by holding the affected part with the pair of the arm portions and by subsequently supplying a high-frequency electric current to the pair of the arm portions, it is possible to efficiently carry out treatment of the thus-held part.

In the aforesaid conventional endoscopic treatment instrument, by slenderizing or thinning the arm portions, the contact area with respect to an object to be treated can be minimized and the current density can be raised. However, the force required for holding the object to be treated is inevitably decreased.

SUMMARY OF THE INVENTION

The present invention has an aim of providing an endoscopic treatment instrument in which the energy density with respect to the object to be treated can be increased while maintaining the holding or gripping force with respect to the object to be treated.

According to the present invention, there is provided an endoscopic treatment instrument comprising: a sheath having electrical insulating properties; a pair of arm portions which are disposed opposite to each other, which protrude and retract with respect to the sheath, and which accordingly open and close to thereby hold an object to be treated; and an energy treating portion which protrudes from and is fixed to the distal end of the sheath and which supplies predetermined energy when it touches the object to be treated.

Preferably, the energy treating portion includes a bent portion which is extended in a direction orthogonal to a central axis of the sheath and positioned at the halfway point between the distal end face of the sheath and the distal end faces of the pair of the arm portions when they have been maximally protruded.

Further, preferably, the endoscope treatment instrument further comprises: an extension and retraction force transmitting portion which transmits to the pair of the arm portions an extension and retraction force with respect to the sheath to open and close the arm portions; an energy leading portion through which said energy is transmitted to the energy treating portion; a first through-hole which is provided in the sheath and through which the extension and retraction force transmitting portion is extendably and retractably inserted; and a second through-hole which is provided in the sheath separately from the first through-hole and through which the energy leading portion is inserted.

Still further, preferably, at least two energy treating portions are provided.

Yet further, preferably, the energy is also transmitted to the pair of the arm portions through the extension and retraction force transmitting portion.

The above and other objects, features, and advantages of the present invention will become more apparent from the following description taken in conjunction with the accompanying drawings.

DETAILED DESCRIPTION OF THE INVENTION

With reference to FIGS. 1 to 10, a description will be given of a first embodiment according to the present invention. As illustrated in FIGS. 1 to 4, a forked (two-pronged) cutting forceps (endoscopic treatment instrument) 1 is provided with a sheath 2 having electrical insulation properties, with a pair of arm portions 3A and 3B which are disposed opposite to each other, which protrude and retract with respect to the sheath 2, and which open and close to thereby hold an object to be treated (or untreated object), with a cutting electrode (energy treating portion) 5 which protrudes from and is fixed to the distal end of the sheath 2 and which supplies a high-frequency electric current (predetermined energy) to an untreated object when it comes in contact with the untreated object, with a control wire (extension and retraction force transmitting portion) 6 which transmits to the pair of the arm portions 3A and 3B extension and retraction force with respect to the sheath 2 to open and close the arm portions 3A and 3B, with an electric cable portion (energy leading portion) 7 through which high-frequency electric current is transmitted to the cutting electrode 5, and with a control portion 8 to which the sheath 2, the control wire 6, and the electric cable portion 7 are connected.

Figure 5:
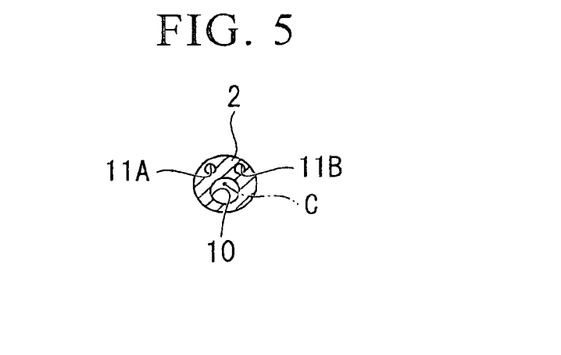
FIG. 5 is a cross-sectional view of a sheath of the forked cutting forceps according to the first embodiment of the present invention.

As illustrated in FIG. 5, the sheath 2 is provided with a lumen for wire insertion (first through-hole) 10 through which the control wire 6 is extendably and retractably inserted and with lumens for electrode insertion (second through-holes) 11A and 11B through which the electric cable 7 is inserted. The central axis of the lumen for wire insertion 10 is displaced with respect to the central axis C of the sheath 2. The lumens for electrode insertion 11A and 11B are disposed remotely from the lumen for wire insertion 10.

Figure 2:
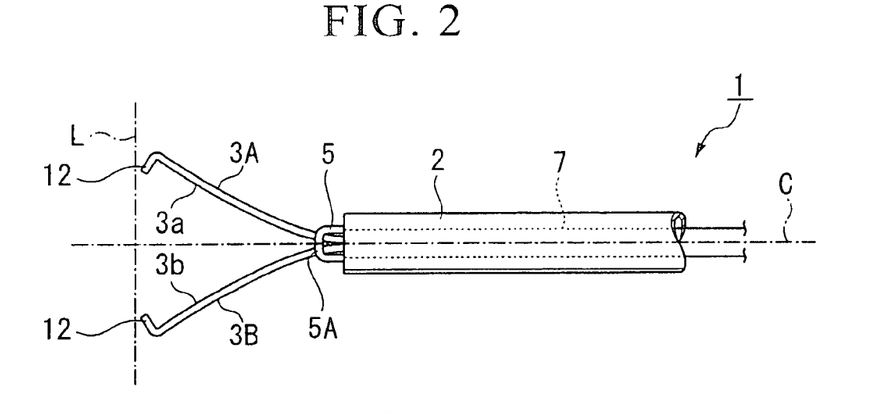
FIG. 2 is a plan view illustrating an important part of the forked cutting forceps according to the first embodiment of the present invention.
Figure 3:
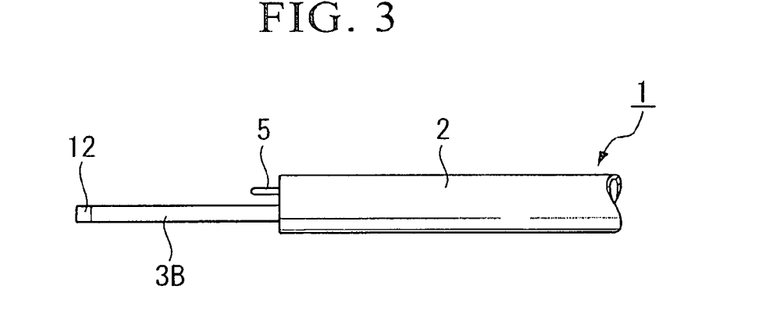
FIG. 3 is a lateral view illustrating the important part of the forked cutting forceps according to the first embodiment of the present invention.
Figure 4:
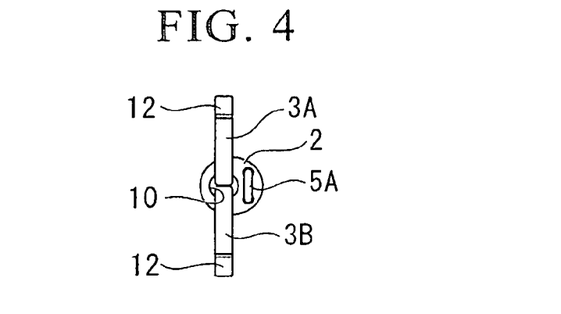
FIG. 4 is a frontal view illustrating the important part of the forked cutting forceps according to the first embodiment of the present invention.

The pair of the arm portions 3A and 3B which are made of a resilient material are formed symmetrically with respect to the central axis C of the sheath 2 and have opposing surfaces 3a and 3b, each of which is formed in a generally L shape. The proximal end side portions thereof are straight and connected to the control wire 6 and the middle portions thereof are slightly arched. On the distal end side portions of the pair of the arm portions 3A and 3B, hooked portions (convex portions) 12 are provided extending toward the central axis C. The outer surfaces of the arm portions 3A and 3B are coated with a predetermined material to form insulating layers (not illustrated).

Figure 1:
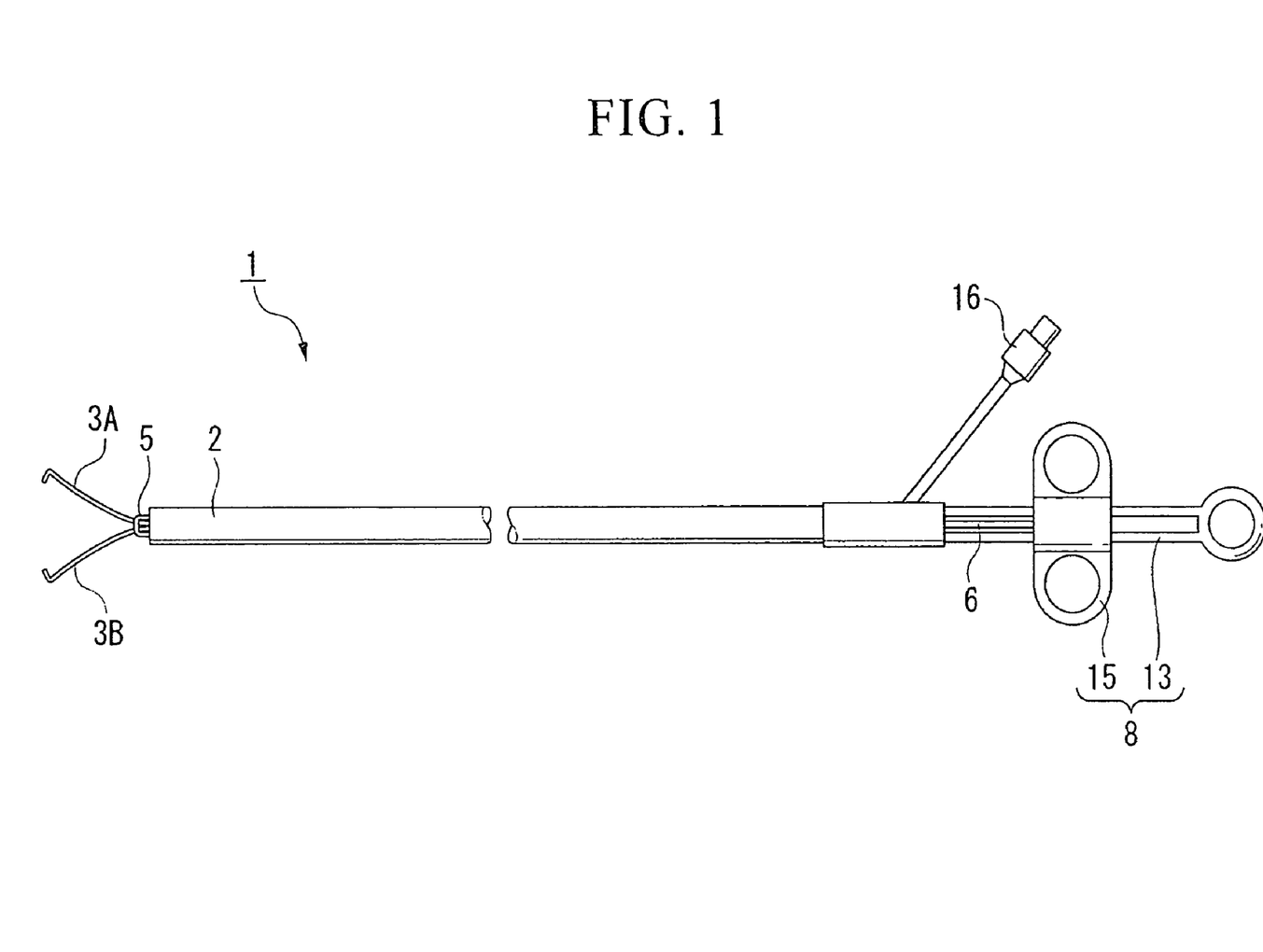
FIG. 1 is a general schematic view illustrating a forked cutting forceps according to a first embodiment of the present invention.

The cutting electrode 5 is bent and formed into a generally C-shape with a linear portion which is extended in a direction orthogonal to the central axis C of the sheath 2 and positioned at the halfway position between a lengthwise position of the distal end face of the sheath and a lengthwise position of the distal end faces of the pair of the arm portions when they have been maximally protruded (maximum protruded position L). The aforesaid linear portion of the cutting electrode 5, which is extended in the direction orthogonal to the central axis C of the sheath 2 or in an opening and closing direction of the arm portions 3A and 3B, forms a cutter portion 5A The control portion 8 is provided with a control portion main body 13 to which the proximal end of the sheath 2 is connected and a slider 15 to which the proximal end of the control wire 6 is connected, and which are extendable and retractable (or advanceable and retreatable) with respect to the control portion main body 13. On the distal end side of the control portion main body 13, an electrode terminal 16 is formed in an extended manner, one end of which is connected to the proximal end of the electric cable portion 7, the other end of which is connectable to an unillustrated high-frequency power supply or source.

Next, with reference to FIGS. 6 to 10, a description will be given of an operation of the forked cutting forceps 1 according to the present embodiment when used in a polyp-extracting operation as one example.

Figure 6:
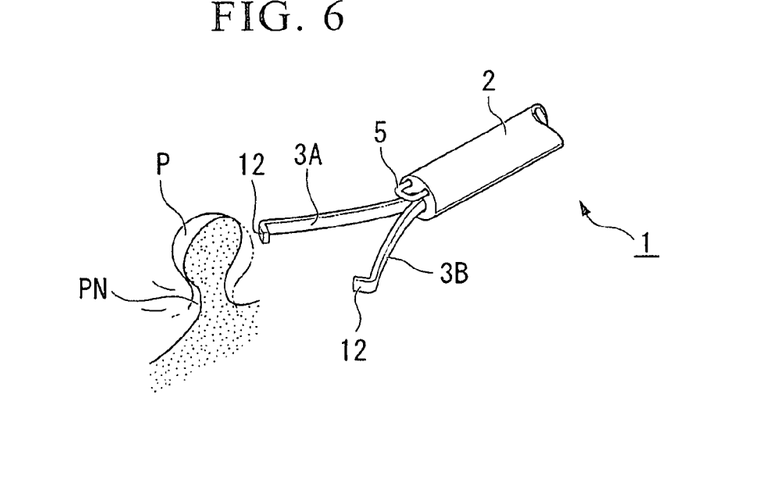
FIG. 6 is a perspective view explaining an operational state of the forked cutting forceps according to the first embodiment of the present invention.

Firstly, an unillustrated reusable electrode is fitted on the patient and then an insertion section (not illustrated) of the endoscope is positioned in the vicinity of a polyp, and thereafter, the sheath 2 of the forked cutting forceps 1 protrudes from the insertion section of the endoscope. Then, an electrode terminal is connected to the high-frequency power supply, and thereafter, the control wire 6 together with the slider 15 are moved toward the distal end side of the sheath 2 with respect to the control portion main body 13. At this time, as illustrated in FIG. 6, the pair of the arm portions 3A and 3B expand because they are released from the binding force of the sheath 2.

Figure 7:
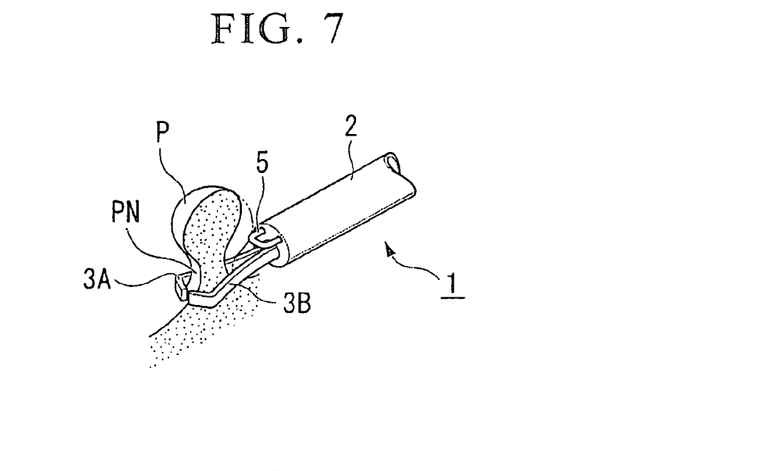
FIG. 7 is a perspective view explaining a further operational state of the forked cutting forceps according to the first embodiment of the present invention.

Subsequently, the arm portions 3A and 3B are positioned so as to sandwich the polyp P, and then, the control wire 6 is moved together with the slider 15 toward the proximal end of the sheath 2 with respect to the control portion main body 13. At this time, as illustrated in FIG. 7, the pair of the arm portions 3A and 3B is pulled in the sheath 2 so that the polyp P is enclosed (encircled) or held by the opposing surfaces 3a and 3b and the hooked portions 12.

Figure 8:
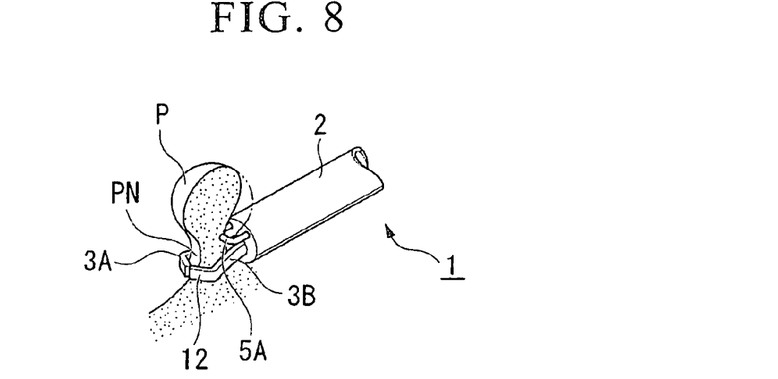
FIG. 8 is a perspective view explaining a yet further operational state of the forked cutting forceps according to the first embodiment of the present invention.
Figure 9:
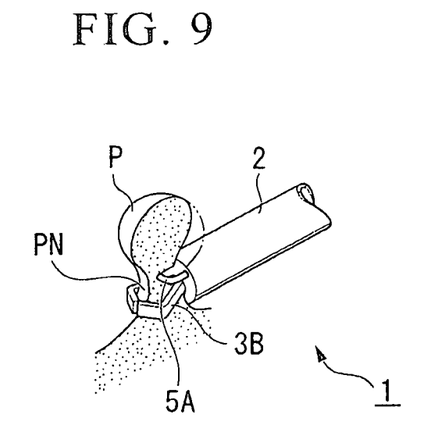
FIG. 9 is a perspective view explaining a still further operational state of the forked cutting forceps according to the first embodiment of the present invention.

As illustrated in FIG. 8, when the control wire 6 is pulled in the sheath 2, a cutter portion 5A of the cutting electrode 5 contacts a neck portion PN of the polyp P. By supplying a high-frequency current from the high-frequency power supply, the cutting electrode 5 and the reusable electrode are electrified. Then, a cutting operation with respect to the neck portion PN where the electrical current density is greatly induced is started. By further pulling or drawing the control wire 6 toward the operator's hand side, the cutting operation advances, as illustrated in FIG. 9. As described, the pair of the arm portions 3A and 3B is further pulled and completely received in the sheath 2, and then, the cutting operation of the polyp P is finished.

Figure 10:
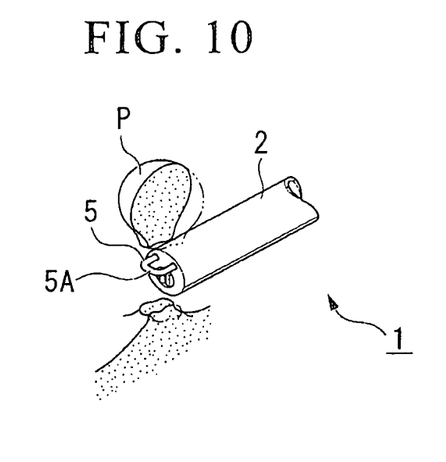
FIG. 10 is a perspective view explaining a different operational state of the forked cutting forceps according to the first embodiment of the present invention.

With the thus-structured forked cutting forceps 1, by protruding (the pair of) the arm portions 3A and 3B from the sheath 2 and by subsequently retracting the same in the sheath 2 while placing the polyp P therebetween, it is possible to hold the polyp P by the pair of the arm portions 3A and 3B and to press the polyp P against the cutter portion 5A of the cutting electrode 5 to thereby cut the polyp P. In this embodiment, the pair of the arm portions 3A and 3B for holding an object to be treated such as the polyp P or the like and the cutting electrode 5 for cutting the object to be treated with the aid of a high-frequency current flow are separately or individually provided. Due to this, even if the holding area by the pair of the arm portions 3A and 3B is increased such that the contact area with respect to the polyp P is increased, it is possible to minimize the cross-sectional area of the cutting electrode 5 and to maintain the current density in a suitable state. In other words, the amount of holding force for holding the object to be treated such as the polyp P and the like can be maintained at an appropriate level, and at the same time, current density with respect to the object to be treated can be raised.

When the pair of the arm portions 3A and 3B protrudes from the sheath 2 and retracted in the sheath 2 while holding the polyp P, it is possible to press the polyp P against the cutting electrode 5 in the middle of the retraction of the pair of the arm portions 3A and 3B. Further, within the sheath 2, it is possible to electrically insulate the control wire 6 and the electric cable portion 7.

Figure 11:
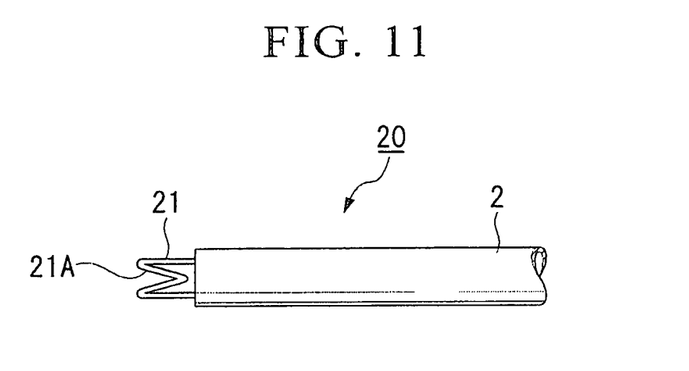
FIG. 11 is a plan view illustrating an important part of a forked cutting forceps according to a second embodiment of the present invention.

Next, with reference to FIG. 11, a description will be given of a second embodiment of the present invention. It should be noted that components which are the same or equivalent as those of the above-mentioned first embodiment are assigned the same reference numerals and that duplicate descriptions are omitted. The second embodiment is different from the first embodiment in that a forked cutting forceps 20 according to the second embodiment has a cutting electrode 21 formed with a cutter portion 21A which has the general shape of an "M" standing upright on the sheath distal end face.

With this forked cutting forceps 20, when the cutter portion 21A is brought into contact with the object to be treated, it is possible for the cutter portion 21A to contact with or abut against the object to be treated in a further stable manner as compared to the case where the cutter portion 21A is formed in a linear shape.

Next, with reference to FIG. 12 to 16, a description will be given of a third embodiment according to the present invention. It should be noted that components which are the same or equivalent as those of the above-mentioned first and second embodiments are assigned the same reference numerals and that duplicate descriptions are omitted. The third embodiment is different from the first embodiment in that, as illustrated in FIGS. 12 to 15, in a forked cutting forceps 30 according to the third embodiment, a first cutting electrode (energy treating portion) 33 and a second cutting electrode (energy treating portion) 35 are provided at positions which are symmetrical in relation to a pair of arm portions 31A and 31B, and the extending directions of cutter portions 33A and 33B of the first and second cutting electrode coincide with an opening/closing direction of the pair of the arm portions 31A and 31B. In short, the forceps including the first cutting electrode 33 and the second cutting electrode 35 is of the bipolar type.

Figure 16:
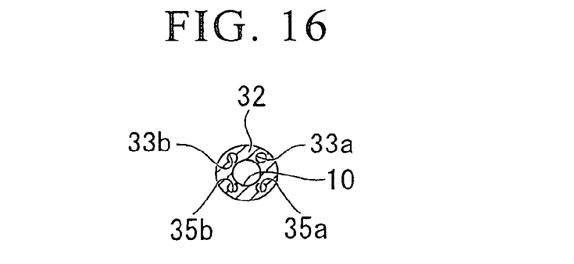
FIG. 16 is a cross-sectional view of a sheath of the forked cutting forceps according to the third embodiment of the present invention.

The sheath 32 is formed with a lumen for wire insertion (first through-hole) 10 that extends along a central axis C, as illustrated in FIG. 16. A lumen for first electrode insertion (second through-hole) 33a and 33b through which a first electric cable portion (electric cable portion) 34 connected to the first cutting electrode 33 is inserted, and a lumen for second electrode insertion (second through-hole) 35a and 35b through which an unillustrated second electric cable portion connected to the second cutting electrode 35 is inserted are provided the lumen for wire insertion 10.

Figure 12:
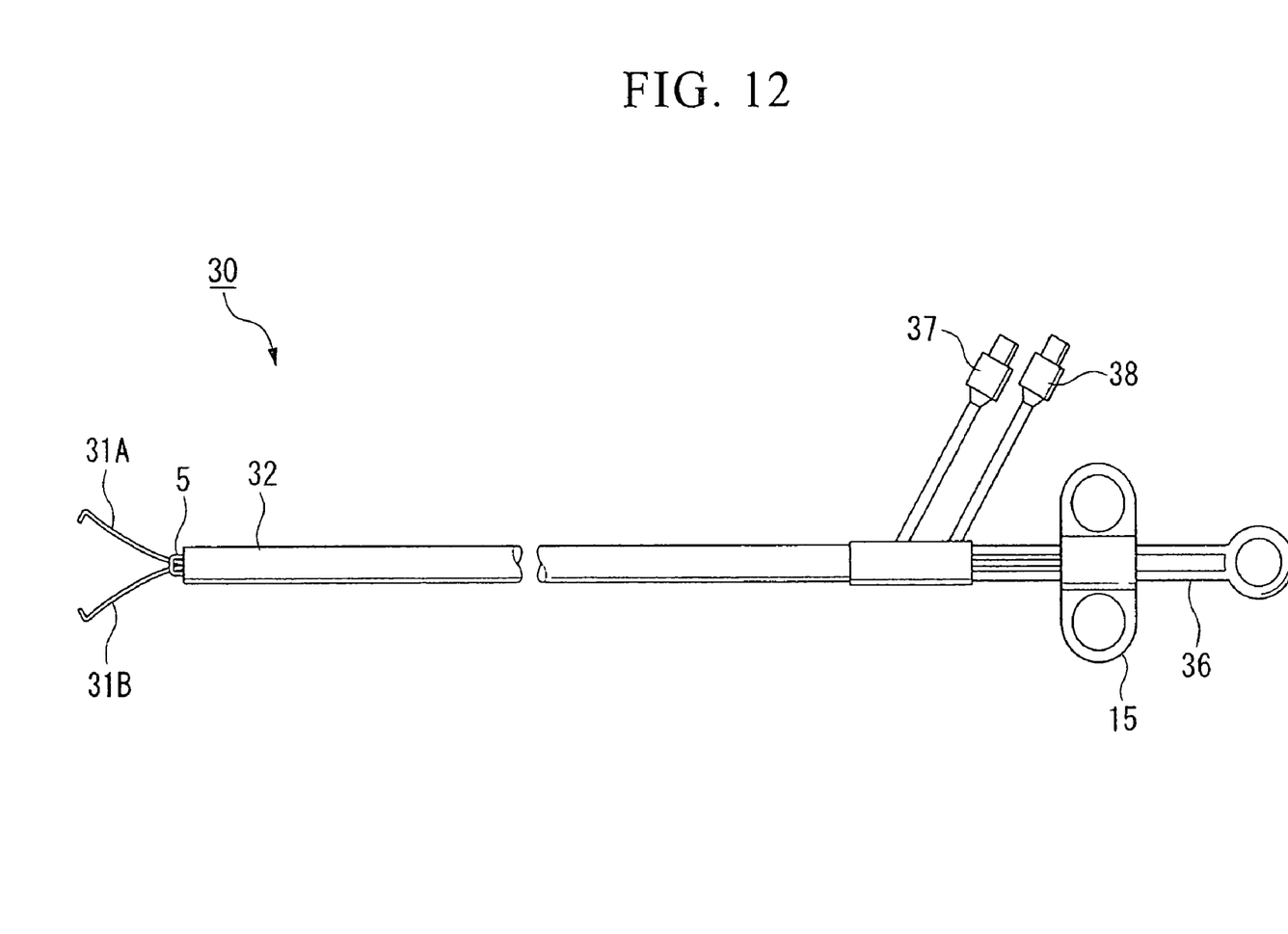
FIG. 12 is a general schematic view illustrating a forked cutting forceps according to a third embodiment of the present invention.

A control portion main body 36 is formed with a first electrode terminal 37 electrically connected to the first cutting electrode 33 and a second electrode terminal 38 electrically connected to the second cutting electrode 35.

Next, a description will be given of an operation of the forked cutting forceps 30 according to the third embodiment when used in a polyp P extracting operation as one example.

Firstly, an insertion section of the endoscope (not illustrated) is positioned in the vicinity of a polyp P and thereafter, the sheath 32 of the forked cutting forceps 30 protrudes from the insertion section of the endoscope. Then, the first electrode terminal 37 and the second electrode terminal 38 are connected to the high-frequency power supply, and thereafter, the control wire 6 is moved toward the distal end side of the sheath 32 and the pair of the arm portions 31A and 31B is expanded or opened.

Figure 13:
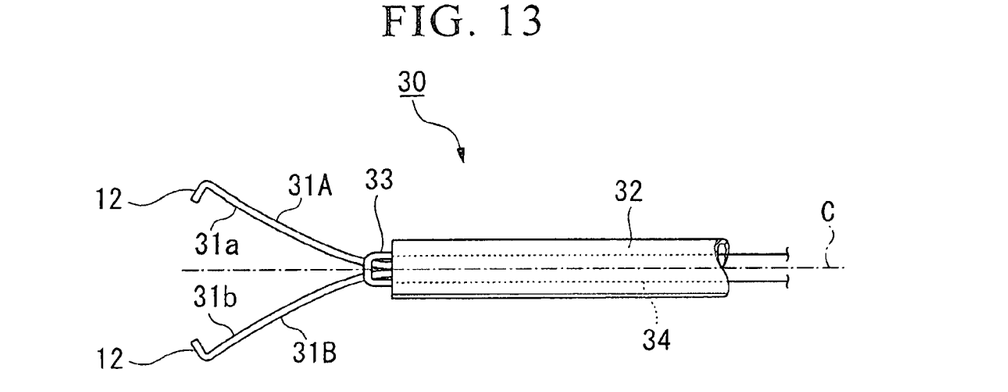
FIG. 13 is a plan view illustrating an important part of the forked cutting forceps according to the third embodiment of the present invention.
Figure 14:
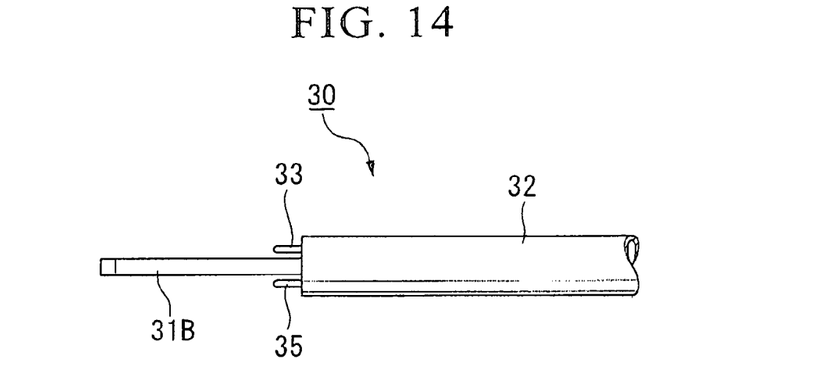
FIG. 14 is a lateral view illustrating the important part of the forked cutting forceps according to the third embodiment of the present invention.
Figure 15:
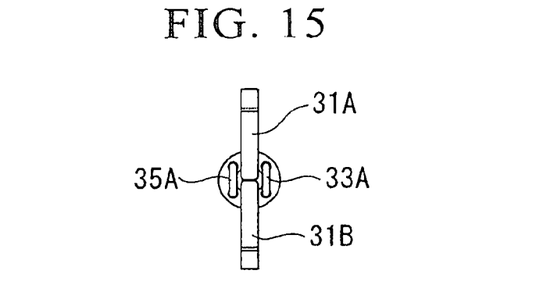
FIG. 15 is a frontal view illustrating the important part of the forked cutting forceps according to the third embodiment of the present invention.

Subsequently, the arm portions 31A and 31B are positioned so as to sandwich the polyp P, and then, the control wire 6 is moved toward the proximal end of the sheath 32. At this time, the pair of the arm portions 31A and 31B is pulled or drawn in the sheath 32 so that the polyp P is encircled and held by opposing surfaces 31a and 31b and hooked portions 12.

As the control wire 6 is pulled in the sheath 32, the cutter portions 33A and 35A of the first and second cutting electrode 33 and 35 contact a neck portion PN of the polyp P. By supplying a high-frequency current from the high-frequency power supply, the first cutting electrode 33 and the second cutting electrode 35 are electrified. Then, a cutting operation with respect to the neck portion PN where the electrical current density is greatly induced is started. The pair of the arm portions 31A and 31B is further pulled and received in the sheath 32, and then, the cutting operation of the polyp P is finished.

With the present forked cutting forceps 30, when, for example, the first cutting electrode 33 is defined as an active electrode and the second cutting electrode 35 is defined as a return electrode, by supplying thereto a high-frequency electric current, it is possible to only electrify the object to be treated which is positioned between the first cutting electrode 33 and the second cutting electrode 35. Accordingly, it is not necessary to fit the reusable electrode on the patient's body, and the degree of freedom in operations or procedures can be improved.

Next, with reference to FIG. 17 to 20, a description will be given of a fourth embodiment according to the present invention. It should be noted that components which are the same or equivalent as those of the above-mentioned first, second, and third embodiments are assigned the same reference numerals and that duplicate descriptions are omitted. The fourth embodiment is different from the first embodiment in that, in a forked cutting forceps 40 according to the fourth embodiment, a high-frequency current is also supplied to a pair of arm portions 41A and 41B through a control wire 42.

Figure 17:
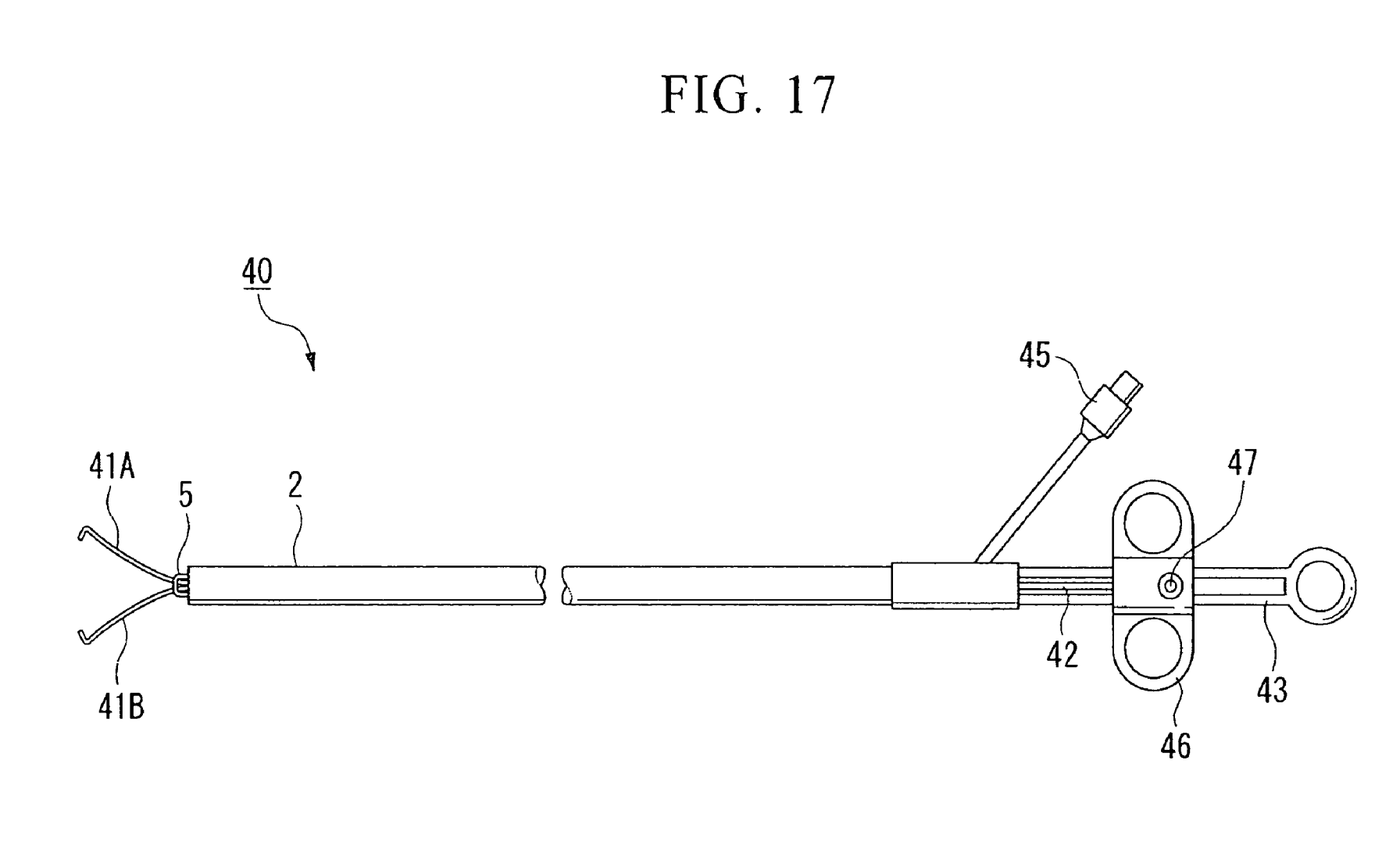
FIG. 17 is a general schematic view illustrating a forked cutting forceps according to a fourth embodiment of the present invention.
Figure 18:
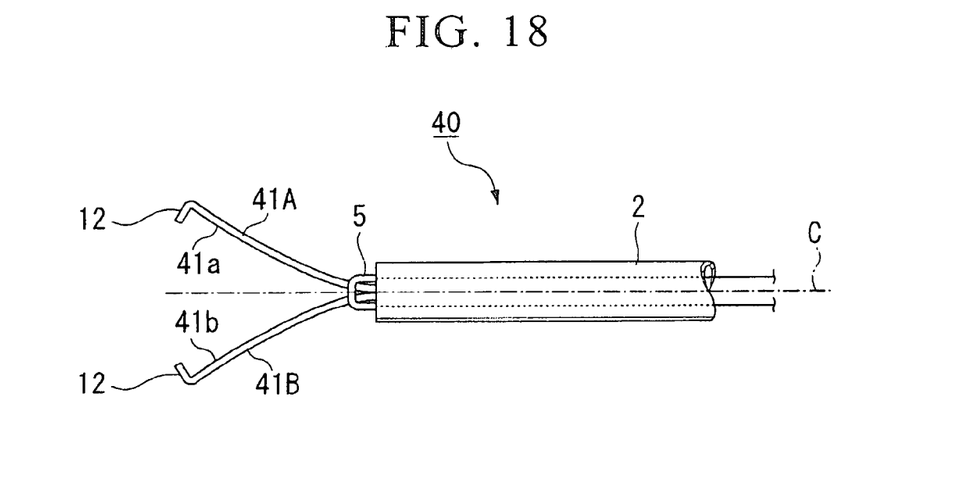
FIG. 18 is a plan view illustrating an important part of the forked cutting forceps according to the fourth embodiment of the present invention.
Figure 19:
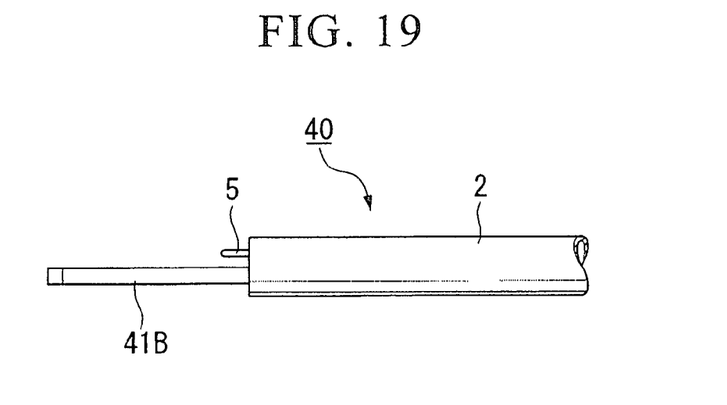
FIG. 19 is a lateral view illustrating the important part of the forked cutting forceps according to the fourth embodiment of the present invention.
Figure 20:
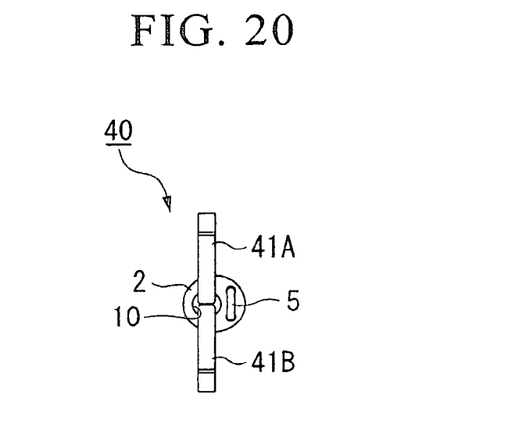
FIG. 20 is a frontal view illustrating the important part of the forked cutting forceps according to the fourth embodiment of the present invention.

Similarly to the forked cutting forceps 30 according to the third embodiment, the forked cutting forceps 40 according to the fourth embodiment is of the bipolar type. Thus, the surfaces of the pair of the arm portions 41A and 41B are conduction surfaces.

A control portion main body is formed with a first electrode terminal 45 that is electrically connected to the cutting electrode 5. A slider 46 is formed with a second electrode terminal 47 that is electrically connected to the pair of the arm portions 41A and 41B through the control wire 42.

Next, a description will be given of an operation of the forked cutting forceps 40 according to the fourth embodiment when used in a polyp P extracting operation as one example.

Firstly, an insertion section of the endoscope (not illustrated) is positioned in the vicinity of the polyp P, and thereafter, the sheath 2 protrudes from the insertion section of the endoscope. Then, the first electrode terminal 45 and the second electrode terminal 47 are connected to the high-frequency power supply, and thereafter, the control wire 42 is moved toward the distal end side of the sheath 2 and the pair of the arm portions 41A and 41B is expanded or opened.

Subsequently, the arm portions 41A and 41B are positioned so as to sandwich the polyp P, and then, the control wire 42 is moved toward the proximal end of the sheath 2. At this time, the pair of the arm portions 41A and 41B is pulled or drawn in the sheath 2 so that the polyp P is enclosed and held by opposing surfaces 41a and 41b and the hooked portions 12.

When the control wire 42 is pulled in the sheath 2, the cutter portion 5A of the cutting electrode 5 contacts or abuts a neck portion of the polyp P. By supplying a high-frequency current from the high-frequency power supply, the cutting electrode 5 and the pair of arm portions 41A and 41B are electrified. Then, a cutting operation with respect to the neck portion where the electrical current density is greatly induced is started. The pair of the arm portions 41A and 41B is further pulled and received in the sheath 2, and then, the cutting operation of the polyp P is finished.

With this forked cutting forceps 40, it is possible to achieve an effect similar to that of the forked cutting forceps 30 according to the third embodiment. Accordingly, it is possible to make the structure simpler than that of the forked cutting forceps according to the third embodiment.

Incidentally, the invention is not limited to the present embodiments illustrated and described herein. It should be understood that various changes and modifications may be made therein without departing from the scope of the present invention.

Figure 21:
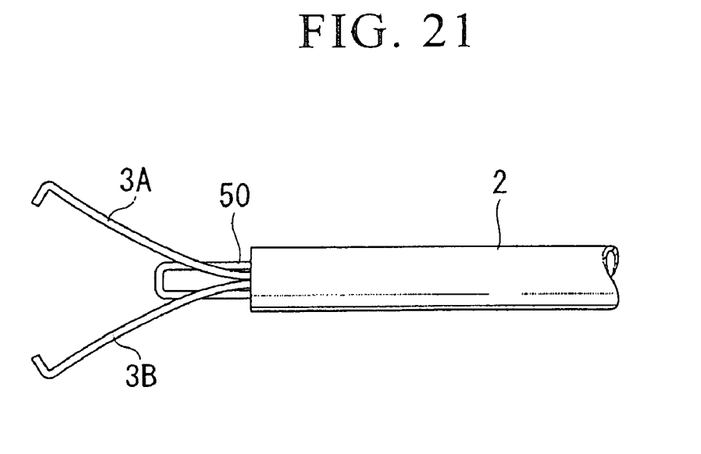
FIG. 21 is a plan view illustrating an important part of a modified example of the forked cutting forceps according to the first embodiment of the present invention.
Figure 22:
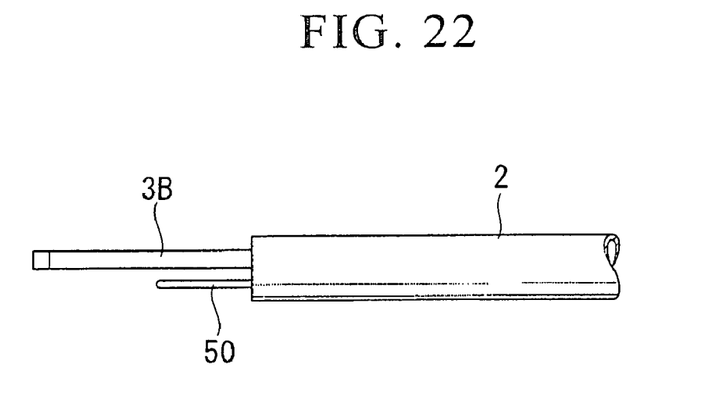
FIG. 22 is a lateral view illustrating the important part of the modified example of the forked cutting forceps according to the first embodiment of the present invention.
Figure 23:
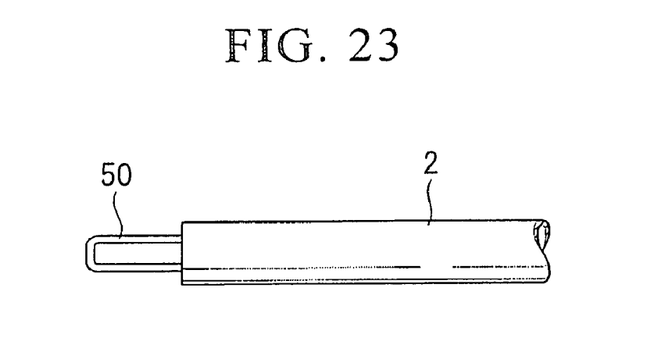
FIG. 23 is a lateral view illustrating an important part of another modified example of the forked cutting forceps according to the first embodiment of the present invention.

For example, each of the embodiments mentioned above describes, as an endoscopic treatment instrument, a cutting forceps in which an object to be treated is held by a pair of arm portions (which are opened and closed). Alternatively, instead of opening and closing the pair of the arm portions 3A and 3B as illustrated in FIGS. 21 and 22, a structure is possible in which only the cutting electrode 50 protrudes from the end face of the sheath 2 and is used as a high frequency knife.

Instead of providing a forked (two-pronged) cutting forceps such as that of the embodiments mentioned above, a three-pronged (forked) cutting forceps or a cutting forceps having four or more arm portions may be provided.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

What is claimed is:

1. An endoscopic treatment instrument comprising:
a sheath having electrical insulating properties;
a pair of arm portions which are disposed opposite to each other, which protrude and retract with respect to the sheath, and which accordingly open and close to thereby hold an object to be treated; and
an energy treating portion which protrudes from and is immovably fixed to the distal end of the sheath and which supplies predetermined energy when it touches the object to be treated,
wherein the energy treating portion includes a bent portion which is extended in a direction orthogonal to a central axis of the sheath and positioned between the distal end face of the sheath and the distal end faces of the pair of the arm portions when they have been maximally protruded.

2. The endoscopic treatment instrument as recited in claim 1, further comprising:
an extension and retraction force transmitting portion which transmits to the pair of the arm portions an extension and retraction force with respect to the sheath to open and close the arm portions;
an energy leading portion through which said energy is transmitted to the energy treating portion;
a first through-hole which is provided in the sheath and through which the extension and retraction force transmitting portion is extendably and retractably inserted; and
a second through-hole which is provided in the sheath separately from the first through-hole and through which the energy leading portion is inserted.

3. The endoscopic treatment instrument as recited in claim 1, wherein at least two energy treating portions are provided.

4. The endoscopic treatment instrument as recited in claim 2, wherein the energy is also transmitted to the pair of arm portions through the extension and retraction transmitting portion.

5. The endoscopic treatment instrument as recited in claim 1, wherein the sheath is provided with a lumen for wire insertion (first through-hole) through which a control wire for controlling retraction of the pair of arm portions is extendably and retractably inserted and with lumens for electrode insertion (second through-holes) through which an electric cable is inserted for providing electrical energy to the energy treating portion, and wherein the central axis of the lumen for wire insertion is axially offset with respect to the central axis of the sheath and the lumens for electrode insertion are disposed remotely from the lumen for wire insertion.

6. An endoscopic treatment instrument comprising:
a sheath having electrical insulating properties;
a pair of arm portions which are disposed opposite to each other, which protrude and retract with respect to the sheath, and which accordingly open and close to thereby hold an object to be treated; and
an energy treating portion which protrudes from and is immovably fixed to the distal end of the sheath and which supplies a predetermined amount of energy when it touches the object to be treated,
the energy treating portion has a cutting electrode formed with a cutter portion which substantially has a shape of an "M" standing upright on the sheath distal end face and positioned between the distal end face of the sheath and the distal end faces of the pair of the arm portions when they have been maximally protruded.

* * * * *